United States Patent [19]

Thomas et al.

[11] Patent Number: 4,756,764
[45] Date of Patent: Jul. 12, 1988

[54] TRICYLIC KETONE AND USE OF SAME AS FLAVORING INGREDIENT

[75] Inventors: Alan F. Thomas, Borex/Vaud; Alistair Y. Smith, Geneva, both of Switzerland

[73] Assignee: Firmenich SA, Geneva, Switzerland

[21] Appl. No.: 19,289

[22] Filed: Feb. 26, 1987

[30] Foreign Application Priority Data

Mar. 3, 1986 [CH] Switzerland .............................. 856/86

[51] Int. Cl.$^4$ ...................... A24B 15/30; C07C 49/643
[52] U.S. Cl. ..................................... 131/276; 568/373; 568/379
[58] Field of Search ................. 568/393, 379; 131/276

[56] References Cited

U.S. PATENT DOCUMENTS 3,351,645  11/1967  Caldwell et al. .................... 568/379
4,318,863   3/1982  Sprecker et al. .................... 568/373

Primary Examiner—James H. Reamer
Attorney, Agent, or Firm—Pennie & Edmonds

[57] ABSTRACT 3,10-Diacetyl-11-isopropylidene-7,7-dimethyl-tricyclo[6.2.1.0$^{2,6}$]undeca-2,5,9-triene is a flavoring ingredient useful for the aromatization of smoking articles. It develops upon smoking green, slightly floral, metallic, astringent, fatty, slightly bitter and earthy notes.

It is prepared by a two-step process from 1-(4-isopropylidene-1-cyclopent-1-enyl)-1-ethanone.

3 Claims, No Drawings

TRICYLIC KETONE AND USE OF SAME AS FLAVORING INGREDIENT

BRIEF SUMMARY OF THE INVENTION

The present invention relates to the field of flavors. More particularly, it provides 3,10-diacetyl-11-isopropylidene-7,7-dimethyl-tricyclo[6.2.1.0$^{2,6}$]undeca-2,5,9-triene, as well as a compound formed during heat transformation of this triene, 2-acetyl-6,6-dimethylfulvene.

The present invention relates further to a method to enhance, improve or modify the aroma and taste of the smoke formed by the combustion of tobacco products which method consists in adding to a base constituted by a tobacco of natural or artificial origin a flavor effective amount of 3,10-diacetyl-11-isopropylidene-7,7-dimethyl-tricyclo[6.2.1.0$^{2,6}$]undeca-2,5,9-triene.

The present invention provides also a process for the preparation of 3,10-diacetyl-11-isopropylidene-7,7-dimethyl-tricyclo[6.2.1.0$^{2,6}$]undeca-2,5,9-triene which process consists in a. oxidizing to air 1-(4-isopropylidene-1-cyclopent-1-enyl)-1-ethanone to give [4-(1-hydroperoxy-1-methylethyl)-1,3-cyclopentadien-1-yl]-1-ethanone, and b. reducing and cyclising the resulting compound by means of a reducing agent.

BACKGROUND OF THE INVENTION

It is well known in the art to utilize a blend of different sorts of tobaccos to manufacture cigarettes so that the resulting articles incorporate the desired and specific flavor character of each one of the tobaccos used. Thus, for instance ordinary cigarettes contain tobaccos of Virginia, Maryland and Kentucky type together with Turkish and oriental tobaccos.

It is also a common practice in the tobacco industry to aromatize tobacco. Its flavor quality can thus be enhanced and stabilized and besides, the quality of the less noble parts of the plant like the ribs can be improved.

This invention provides a novel solution to this problem.

THE INVENTION

We have discovered that 3,10-diacetyl-11-isopropylidene-7,7-dimethyl-tricyclo[6.2.1.0$^{2,6}$]undeca-2,5,9-triene possesses useful organoleptic properties and consequently it could find advantageously a utilization as flavoring ingredient, specially when added to a smoking article, smoking tobacco in particular.

3,10-Diacetyl-11-isopropylidene-7,7-dimethyl-tricyclo[6.2.1.0$^{2,6}$undeca-2,5,9-triene is a new chemical entity. It can be obtained starting from alphaterpineol according to the following reaction scheme.

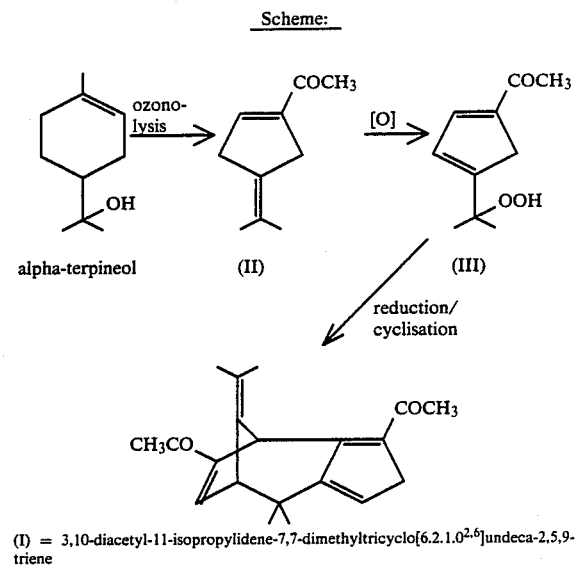

(I) = 3,10-diacetyl-11-isopropylidene-7,7-dimethyltricyclo[6.2.1.0$^{2,6}$]undeca-2,5,9-triene The conversion of alpha-terpineol into 1-(4-isopropylidene-1-cyclopent-1-enyl)-1-ethanone (II) is carried out according to the method described by G. Bozzato et al., J. Chem. Soc., Chem. Comm. (1974), 1005, by ozonolysis in methanol followed by treatment with phosphoric acid.

This invention provides a process for the subsequent transformation of the obtained ethanone (II) into the desired 3,10-diacetyl-11-isopropylidene-7,7-dimethyl-tricyclo[6.2.1.0$^{2,6}$]undeca-2,5,9-triene (I) by way of a two-step reaction.

By simple oxidation in air, preferably in the dark, ethanone (II) is converted into hydroperoxide (III), or [4-(1-hydroperoxy-1-methylethyl)-1,3-cyclo-pentadien-1-yl]-1-ethanone. This latter compound is then reduced to the desired tricyclic ketone by means of a current reducing agent. Suitable reducing agents include an alkali metal iodide or, preferably an aromatic phosphine, such as triphenylphosphine.

3,10-Diacetyl-11-isopropylidene-7,7-dimethyl-tricyclo[6.2.1.0$^{2,6}$]undeca-2,5,9-triene of the invention can be utilized in its isolated form or preferably in admixture with current flavoring coingredients, of both natural and synthetic origin. The man in the art knows by experience the nature of useful coingredients, supports and diluents and it is not here deemed necessary to distinctly enumerate them. Specific examples of useful ingredients can be found in the trade literature such as: S. Arctander, "Perfume and Flavor Chemicals", Montclair, N.J. (1969); G. Fenaroli, "Handbook of Flavor Ingredients", 2nd edition, CRC Press, Inc., Cleveland, Ohio (1975); S. van Straten and H. Maarse, "Volatile Compounds in Food", Institut CIVO-Analysis TNO (1983).

Among the flavoring coingredients more specially destined to tobacco aromatization, it would be useful to mention those described in French Pat. No. 2,175,236.

The proportion at which 3,10-diacetyl-11-isopropylidene-7,7-dimethyltricyclo[6.2.1.0$^{2,6}$]undeca-2,5,9-triene can be used to promote the useful desired organoleptic properties can vary within a wide range of values. They depend on the flavor effect is is desired to achieve and of course on the nature of the product to which they are added. Typical useful effects can be achieved by using proportions of the order of 0.1 to 10 ppm (parts per million) by weight based on the total weight of the flavored material. Preferred proportions are within about 0.1 and 1.0 ppm. These values are not to be interpreted restrictively and they are given as not limitative examples of application.

3,10-Diacetyl-11-isopropylidene-7,7-dimethyl-tricyclo[6.2.1.0$^{2,6}$]undeca-2,5,9-triene is able to develop the scent of leaves or straw and possesses green, slightly floral, metallic, astringent, fatty, slightly bittery and earthy notes. Its taste, when applied to tobacco remains practically unnoticed. It is only when activated by combustion, more specifically through smoking, that it develops its useful character. This phenomenon suggests that the product is heat decomposed to give a flavor effective derivative to which we have assigned the structure of 2-acetyl-6,6-dimethylfulvene

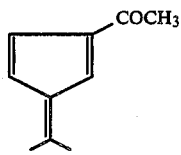

(IV)

Fulvene (IV) is not stable at room temperature and atmospheric pressure. It dimerizes to yield again 3,10-diacetyl-11-isopropylidene-7,7-dimethyl-tricyclo[6.2.1.0$^{2,6}$]undeca-2,5,9-triene.

This phenomenon is certainly positive for the use considered in the instant invention. In effect, for tobacco aromatization flavorists are often confronted to the problem of having to use organoleptically neutral ingredients, which, while odorless at room temperature, develop their interesting properties only on smoking.

The product obtained by decomposition of 3,10-diacetyl-11-isopropylidene-7,7-dimethyl-tricyclo[6.2.1.0$^{2,6}$]undeca-2,5,9-triene, viz. 2-acetyl-6,6-dimethylfulvene, is also a new compound of prior unknown structure.

The invention is illustrated in a more detailed manner by the following examples wherein temperatures are indicated in degrees centigrade and the abbreviations have the meaning common in the art.

EXAMPLE 1

Preparation of 3,10-diacetyl-11-isopropylidene-7,7-dimethyltricyclo[6.2.1.0$^{2,6}$]undeca-2,5,9-triene a. 76 G of 1-(4-isopropylidene-1-cyclopent-1-enyl)-1-ethanone, obtained from 154 g of alpha-terpineol according to G. Bozzato et al., J. Chem. Soc., Chem. Commun. (1974), 1005, crystallized in pentane, were exposed to air in the dark during 3 days.

The product was then crystallized in ether and gave [4-(1-hydroperoxy-1-methylethyl)-1,3-cyclopentadien-1-yl]-1-ethanone having mp. 82°-84°.

UV: lambda$_{max}$ 222 nm (epsilon 6830), 300 nm (epsilon 2120);

IR: 3525, 1690 cm$^{-1}$;

$^1$H-NMR (CDCl$_3$): 1.51 (6H, s); 2.37 (3H, s); 3.42 (2H, d, J=1.5 cps); 6.51 and 7.29 (each 1H) delta ppm;

$^{13}$C-NMR: q at 25.2, 26.0; t at 39.5; d at 128.0, 143.4; s at 81.4, 146.1, 161.7, 194.8;

MS: (M+-H$_2$O): 164 (7); m/z: 149 (100), 121 (40), 93 (32), 77 (27), 43 (30);

Found: C 66.2%; calculated for C$_{10}$H$_{14}$O$_3$ C 65.9% H 7.9% H 7.7% b. 5.7 G of triphenylphosphine were added portionwise to a solution of 4 g of the hydroperoxide obtained sub letter a. above in 20 ml of chloroform. During addition, the temperature of the solution was kept below 25° by external cooling. After one hour, the solution was concentrated and the resulting residue chromatographed on a silica gel column (eluant: ether/pentane 1:1). After elution of 6.4 g of triphenylphosphine oxide, 1.5 g of the desired ketone were eluted. The product had mp. 138-9 after recrystallization in ether.

UV: lambda$_{max}$ 238 nm (epsilon 10500), 305 nm (epsilon 6700);

IR: 1632, 1663 cm$^{-1}$;

$^1$H-NMR: 1.24; 1.25; 1.70; 1.75; 2.27; 2.69 (each 3H, s); system ABX with A 3.12; B 3.20; X 6.29 (J$_{AB}$ 22; J$_{AX}$ and J$_{BX}$ 2.5); 3.21 (1H, d, J=3 cps); 5.16 (1H, s); 7.08 (1H, d, J=3) delta ppm.

A further elution of the silica gel column enabled the isolation of 1.5 g of 3,10-diacetyl-11-isopropylidene-7,7-dimethyl-tricyclo[6.2.1.0$^{2,6}$]-undeca-3,5,9-triene, the mass spectrum of which was identical to that of the 2,5,9-isomeric triene described above.

MS: 148 (57), 133 (100), 105 (50), 103 (20), 79 (28), 77 (30), 63 (12), 51 (14), 43 (13), 39 (10).

By treatment of 0.5 g of the 3,5,9-isomeric triene in 10 ml of ether with basic alumina (Fluka AG, Buchs-activity 1, 0.5 g), the compound was converted into the 2,5,9-isomer.

EXAMPLE 2

3,10-Diacetyl-11-isopropylidene-7,7-dimethyl-tricyclo[6.2.1.0$^{2,6}$]undeca-2,5,9-triene, obtained according to the process described in above Example 1, was injected in a proportion of 0.1 and 1 ppm, respectively, into two samples of commercial cigarettes (type: Marlboro, Philip Morris Co.) in the form of a solution in 95% ethanol. After having been left for 48 hours, the thus aromatized cigarettes were subjected to an organoleptic evaluation by a panel of flavor experts. Their taste and aroma was determined by comparison witn non-flavored identical cigarettes.

At the two dose levels indicated, the smoke of the flavored cigarettes presented a rounder character with a less acidic note than that of the unflavored cigarettes. The smoke had clearly a fuller aromatic character. At the higher dose level, the smoke was sweeter with a caramel- and maple-like nuance. The aroma of the cigarettes before combustion was on the contrary identical in the two cases with that possessed by the unflavored cigarettes.

What we claim is:

1. 3,10-Diacetyl-11-isopropylidene-7,7-dimethyl-tricyclo[6.2.1.0$^{2,6}$]undeca-2,5,9-triene.

2. Method to enhance, improve or modify the aroma and taste of the smoke formed by the combustion of tobacco products which method consists in adding to a base constituted by a tobacco of natural or artificial origin a flavor effective amount of the product according to claim 1.

3. Smoking article containing a flavor effective amount of the product according to claim 1.

* * * * *